(12) United States Patent
Kitano (10) Patent No.: US 10,281,711 B2
(45) Date of Patent: May 7, 2019

(54) ENDOSCOPE WITH RETENTION MEMBER (71) Applicant: FUJIFILM Corporation, Tokyo (JP)

(72) Inventor: Ryo Kitano, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 166 days.

(21) Appl. No.: 15/293,301

(22) Filed: Oct. 14, 2016

(65) Prior Publication Data

US 2017/0108691 A1    Apr. 20, 2017

(30) Foreign Application Priority Data

Oct. 15, 2015 (JP) ................. 2015-203850

(51) Int. Cl.
*A61B 1/05*     (2006.01)
*G02B 23/24*    (2006.01)
*H04N 5/225*    (2006.01)
*A61B 1/00*     (2006.01)
(Continued)

(52) U.S. Cl.
CPC ...... *G02B 23/2484* (2013.01); *A61B 1/00096* (2013.01); *A61B 1/05* (2013.01); *A61B 1/051* (2013.01); *H04N 5/2253* (2013.01); *H04N 5/2256* (2013.01); *A61B 1/0669* (2013.01); *A61B 1/07* (2013.01); *H04N 2005/2255* (2013.01)

(58) Field of Classification Search
CPC ....... A61B 1/051; A61B 1/053; A61B 1/0669; G02B 23/2476; G02B 23/2484; H04N 2005/2255; H04N 5/2253
USPC ...................................... 600/110
See application file for complete search history.

(56) References Cited

U.S. PATENT DOCUMENTS 4,831,456 A    5/1989  Takamura
5,010,642 A *  4/1991  Takahashi ........ H01B 13/01254
                                                  140/147

(Continued)

FOREIGN PATENT DOCUMENTS

JP    S63272180        11/1988
JP    05293080 A  *   11/1993
(Continued)

OTHER PUBLICATIONS

"Search Report of Europe Counterpart Application", dated Mar. 3, 2017, p. 1-p. 12.

(Continued)

*Primary Examiner* — John P Leubecker
*Assistant Examiner* — Shankar R Ghimire
(74) *Attorney, Agent, or Firm* — JCIPRNET (57) ABSTRACT

An endoscope includes an image sensor that is disposed at a front end portion of an insertion portion of the endoscope; a circuit board that is mounted with the image sensor; a plurality of electric wires that are electrically connected to the circuit board; and a retention member that has a retention portion tying up the electric wires; and the retention portion is disposed in a narrowed section that is provided in the insertion portion and inside a part adjacent to the front end portion in an axial direction of the insertion portion and narrowed in a narrowing direction perpendicular to the axial direction so that the electric wires are tied up to be longer in a direction perpendicular to the narrowing direction and the axial direction than in the narrowing direction.

16 Claims, 10 Drawing Sheets (51) Int. Cl.
*A61B 1/06* (2006.01)
*A61B 1/07* (2006.01)

(56) References Cited

U.S. PATENT DOCUMENTS

| | | | | | |
|---|---|---|---|---|---|
| 6,482,149 | B1* | 11/2002 | Torii | ................... | A61B 1/0055 600/141 |
| 7,189,103 | B1* | 3/2007 | Brown | ............... | H01R 43/0263 439/493 |
| 8,679,000 | B2* | 3/2014 | Kimura | .................. | A61B 1/051 600/110 |
| 8,681,207 | B2* | 3/2014 | Tsujimura | .......... | A61B 1/00096 348/65 |
| 8,801,255 | B2* | 8/2014 | Kudo | ................... | A61B 1/0684 362/572 |
| 8,956,279 | B2* | 2/2015 | Kitano | ............... | A61B 1/00096 600/109 |
| 2009/0177038 | A1* | 7/2009 | Yashiro | ................ | A61B 1/0051 600/132 |
| 2009/0223041 | A1* | 9/2009 | Garrison | ................ | H01R 12/63 29/755 |
| 2011/0063428 | A1 | 3/2011 | Sonnenschein et al. | | |
| 2011/0092769 | A1* | 4/2011 | Kokubo | ................... | A61B 1/05 600/109 |
| 2011/0211053 | A1* | 9/2011 | Nakayama | ............. | A61B 1/051 348/76 |
| 2012/0197081 | A1* | 8/2012 | Kimura | .............. | A61B 1/00124 600/110 |
| 2012/0220825 | A1 | 8/2012 | Kimura | | |
| 2013/0085328 | A1* | 4/2013 | Kitano | ............... | A61B 1/00096 600/110 |
| 2014/0157868 | A1* | 6/2014 | Ward | .................... | G01M 15/10 73/23.31 |
| 2014/0191457 | A1* | 7/2014 | Sharma | .................. | H05K 3/301 269/37 |
| 2014/0320621 | A1* | 10/2014 | Sonnenschein | .... | A61B 1/00096 348/76 |
| 2015/0305601 | A1* | 10/2015 | Levi | ................... | A61B 1/00089 600/104 |
| 2016/0166134 | A1 | 6/2016 | Sonnenschein et al. | | |
| 2016/0213227 | A1 | 7/2016 | Osaki et al. | | |

FOREIGN PATENT DOCUMENTS

| | | | |
|---|---|---|---|
| JP | H05-293080 | | 11/1993 |
| JP | H07084193 | | 3/1995 |
| JP | H07108037 | | 4/1995 |
| JP | 2009-131513 | | 6/2009 |
| JP | 2009153902 | | 7/2009 |
| JP | 2009296542 | | 12/2009 |
| JP | 2012170765 | | 9/2012 |
| JP | 2012205807 A | * | 10/2012 |
| JP | 2013504400 | | 2/2013 |
| JP | 2015-024029 | | 2/2015 |
| JP | WO 2015079809 A1 | * | 6/2015 ......... G02B 23/2476 |
| WO | 2015079809 | | 6/2015 |

OTHER PUBLICATIONS

Office Action of Japan Counterpart Application, with English translation thereof, dated Jan. 8, 2019, pp. 1-3.

* cited by examiner

ENDOSCOPE WITH RETENTION MEMBER

CROSS-REFERENCE TO RELATED APPLICATIONS

This application claims the benefit of Japanese Patent Application JP 2015-203850, filed Oct. 15, 2015, the entire content of which is hereby incorporated by reference, the same as if set forth at length.

FIELD OF THE INVENTION

The present invention relates to an endoscope.

BACKGROUND OF THE INVENTION

An imaging device to be mounted on a front end portion of an insertion portion of an endoscope is generally provided with an image sensor and a circuit board on which the image sensor is mounted. A plurality of electric wires inserted into the insertion portion are connected to the circuit board.

In an imaging device disclosed in JP-A-2009-131513, in order to enhance durability in connection between a circuit board and each electric wire, a plurality of electric wires are arranged in a flat shape along a board surface of the circuit board, and coatings of the electric wires are firmly attached to the circuit board through adhesive materials respectively while conductors of the electric wires are connected to lands of the circuit board respectively on the front side from the parts firmly attached to the circuit board.

In addition, in an imaging device disclosed in JP-A-2015-24029, in order to reduce the diameter of an insertion portion, terminal portions of electric wires are arranged in a flat shape, and the terminal portions are tied up in a bundle by a flexible linear member.

SUMMARY OF THE INVENTION

There is a request for further reduction in diameter of an insertion portion of an endoscope. With reduction in diameter of the insertion portion, the inside of the insertion portion is narrowed, and a plurality of electric wires inserted into the insertion portion are disposed densely together with other contents. The electric wires tied up in a bundle are restrained by one another so that the electric wires can be suppressed from scattering individually. Thus, tying up the electric wires is useful for reducing the diameter of the insertion portion, and also useful for suppressing the electric wires from being damaged due to contact with the other contents in the insertion portion.

However, in the imaging device disclosed in JP-A-2015-24029, there is no consideration about the positions and directions with which the electric wires should be arranged in a flat shape and tied up in a bundle in the insertion portion. When a plurality of electric wires are tied up unreasonably in a flat shape, reduction in diameter of the insertion portion may be rather impeded, and damage on the electric wires may be induced.

The present invention has been developed in consideration of the aforementioned situation. An object of the invention is to make it possible to properly tie up a plurality of electric wires to be connected to a circuit board to thereby reduce the diameter of an insertion portion, and to enhance durability.

An endoscope according to an aspect of the invention comprises: an image sensor that is disposed at a front end portion of an insertion portion; a circuit board that is mounted with the image sensor; a plurality of electric wires that are electrically connected to the circuit board; and a retention member that includes a retention portion tying up the electric wires; wherein: the retention portion is disposed in a narrowed section that is provided in the insertion portion and inside a part adjacent to the front end portion in an axial direction of the insertion portion and narrowed in a narrowing direction perpendicular to the axial direction so that the electric wires are tied up to be longer in a direction perpendicular to the narrowing direction and the axial direction than in the narrowing direction.

According to the invention, it is possible to reduce the diameter of an insertion portion of an endoscope, and it is also possible to enhance durability thereof.

DESCRIPTION OF REFERENCE NUMERALS AND SIGNS 1 endoscope system
2 endoscope
3 light source unit
4 processor unit
5 monitor
6 insertion portion
7 operation portion
8 universal cord
9 connector
10 front end portion
11 bent portion
12 soft portion
14 treatment tool channel
20 imaging device
21 image sensor
22 imaging optical system
23 sensor holder
24 circuit board
26 terminal
27 electric wire 28 retention member
33 retention portion
34 cover portion
42 piece
43 pin
120 imaging device
121 connection auxiliary member
122 shield conductor
125 metal foil
126 lock hole
R resin material

DETAILED DESCRIPTION OF THE INVENTION

Figure 1:
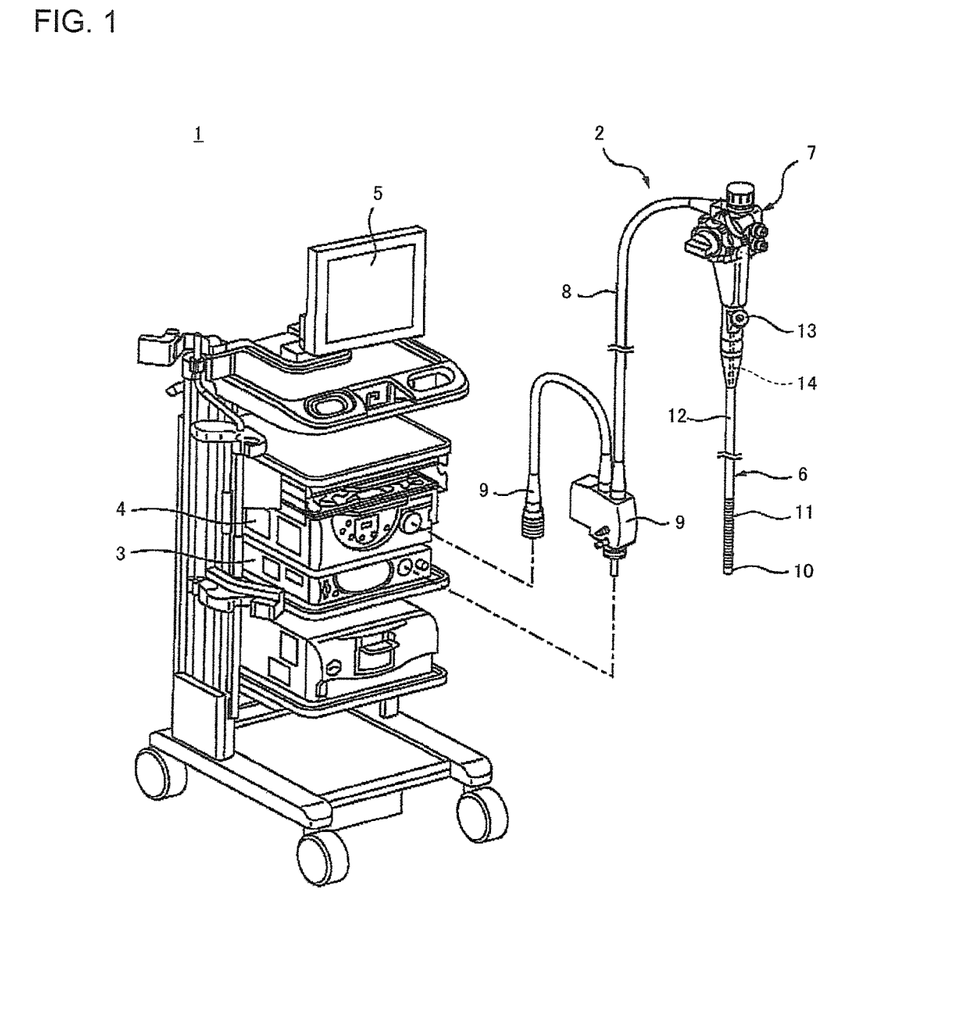
FIG. 1 is a configuration diagram showing an example of an endoscope system for explaining an embodiment of the invention.

FIG. 1 shows an example of an endoscope system for explaining an embodiment of the invention.

An endoscope system 1 has an endoscope 2, a light source unit 3, and a processor unit 4. The endoscope 2 has an insertion portion 6, an operation portion 7, and a universal cord 8. The insertion portion 6 is inserted into a subject to be inspected. The operation portion 7 is connected to the insertion portion 6. The universal cord 8 extends from the operation portion 7. The insertion portion 6 is constituted by a front end portion 10, a bent portion 11, and a soft portion 12. The bent portion 11 is connected to the front end portion 10. The bent portion 11 and the operation portion 7 are connected through the soft portion 12.

The front end portion 10 is provided with an illumination optical system, an imaging device, an imaging optical system, etc. The illumination optical system emits illumination light for lighting a part to be observed. The imaging device and the imaging optical system take an image of the part to be observed. The bent portion 11 is arranged so that it can be bent in a direction perpendicular to the longitudinal axis of the insertion portion 6. The bending operation of the bent portion 11 is operated by the operation portion 7. In addition, the soft portion 12 is arranged to be comparatively soft enough to be deformed following the shape of an insertion path in the insertion portion 6.

The operation portion 7 is provided with a button, a rotary knob, etc. The imaging operation of the imaging device in the front end portion 10 is operated by the button. The bending operation of the bent portion 11 is operated by the rotary knob. An introduction port 13 is also provided in the operation portion 7. A treatment tool such as an electric knife is introduced through the introduction port 13. A treatment tool channel 14 is provided inside the insertion portion 6. The treatment tool channel 14 extends from the introduction port 13 and reaches the front end portion 10. The treatment tool is inserted through the treatment tool channel 14.

A connector 9 is provided at a terminal end of the universal cord 8. The endoscope 2 is connected to the light source unit 3 and the processor unit 4 through the connector 9. The light source unit 3 generates illumination light to be emitted from the illumination optical system in the front end portion 10. The processor unit 4 processes a video signal acquired by the imaging device in the front end portion 10. The processor unit 4 processes the inputted video signal, generates video data of the part to be observed, displays the generated video data on a monitor 5, and records the generated video data.

A light guide and a group of electric wires are received inside the insertion portion 6, the operation portion 7 and the universal cord 8. Illumination light generated by the light source unit 3 is guided to the illumination optical system of the front end portion 10 through the light guide, and signals and electric power are transmitted between the imaging device of the front end portion 10 and the processor unit 4 through the group of electric wires.

Figure 2:
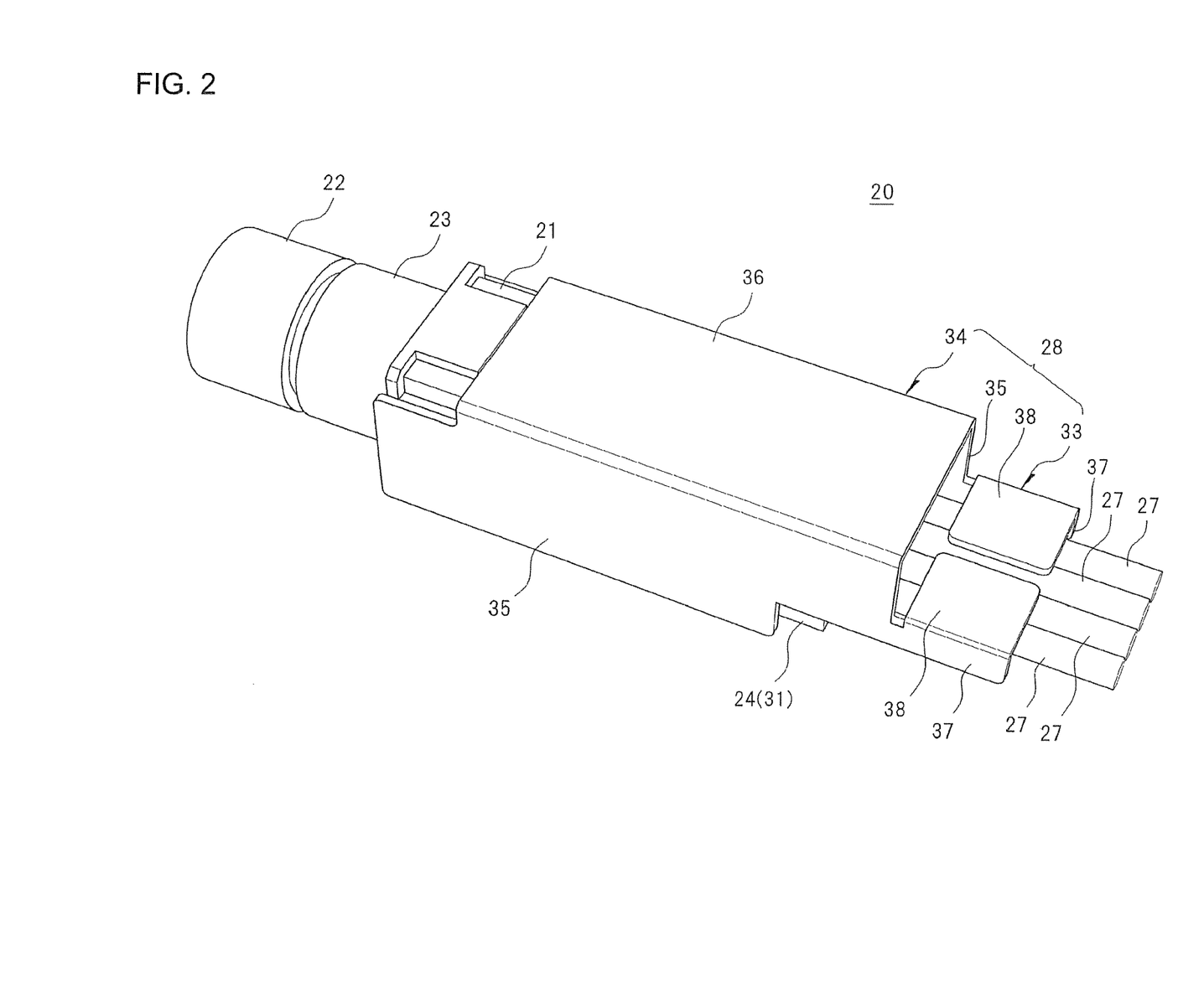
FIG. 2 is a perspective view showing an imaging device mounted on a front end portion of an insertion portion of an endoscope in FIG. 1.
Figure 3:
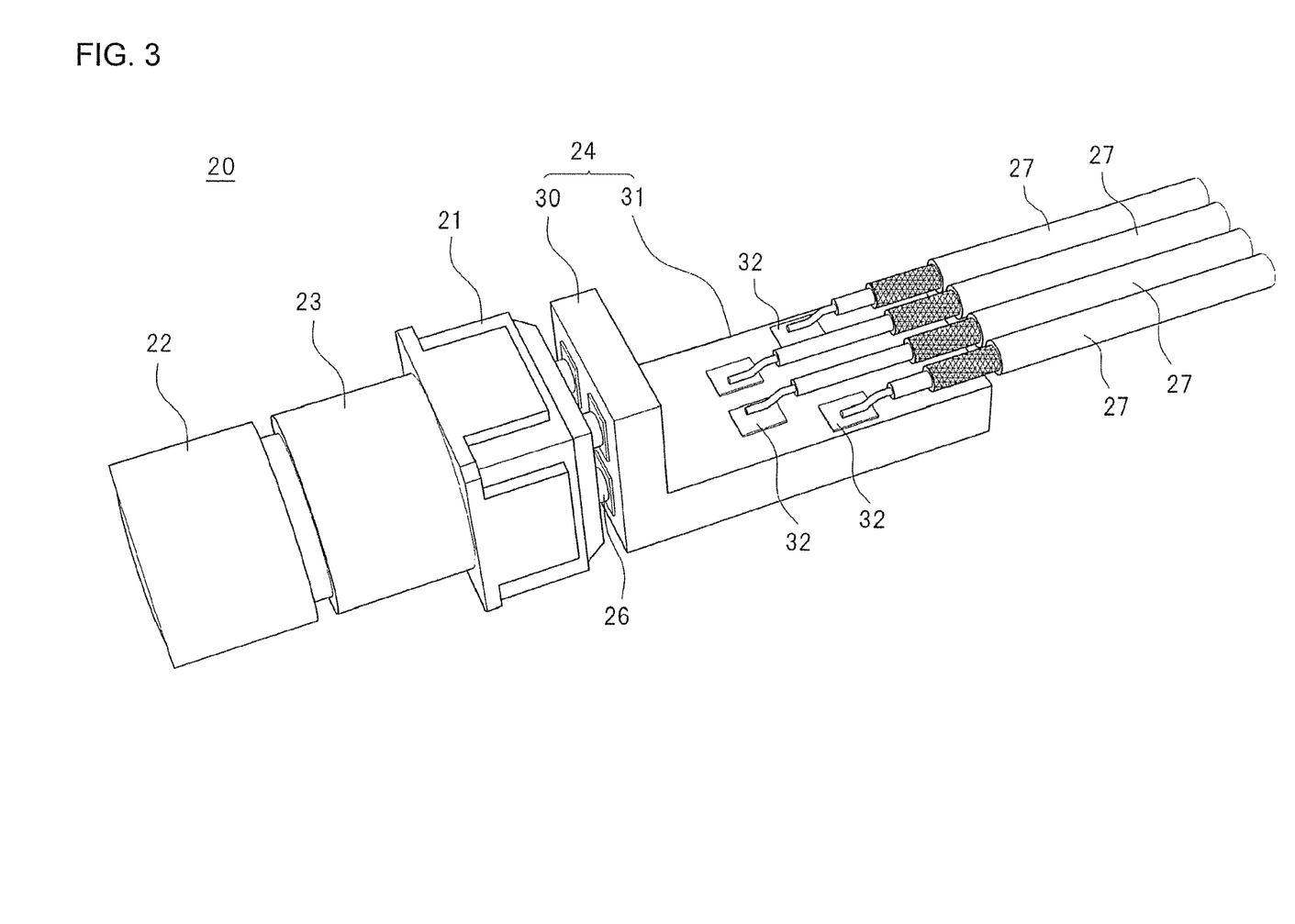
FIG. 3 is a perspective view showing the inside of the imaging device in FIG. 2.
Figure 4:
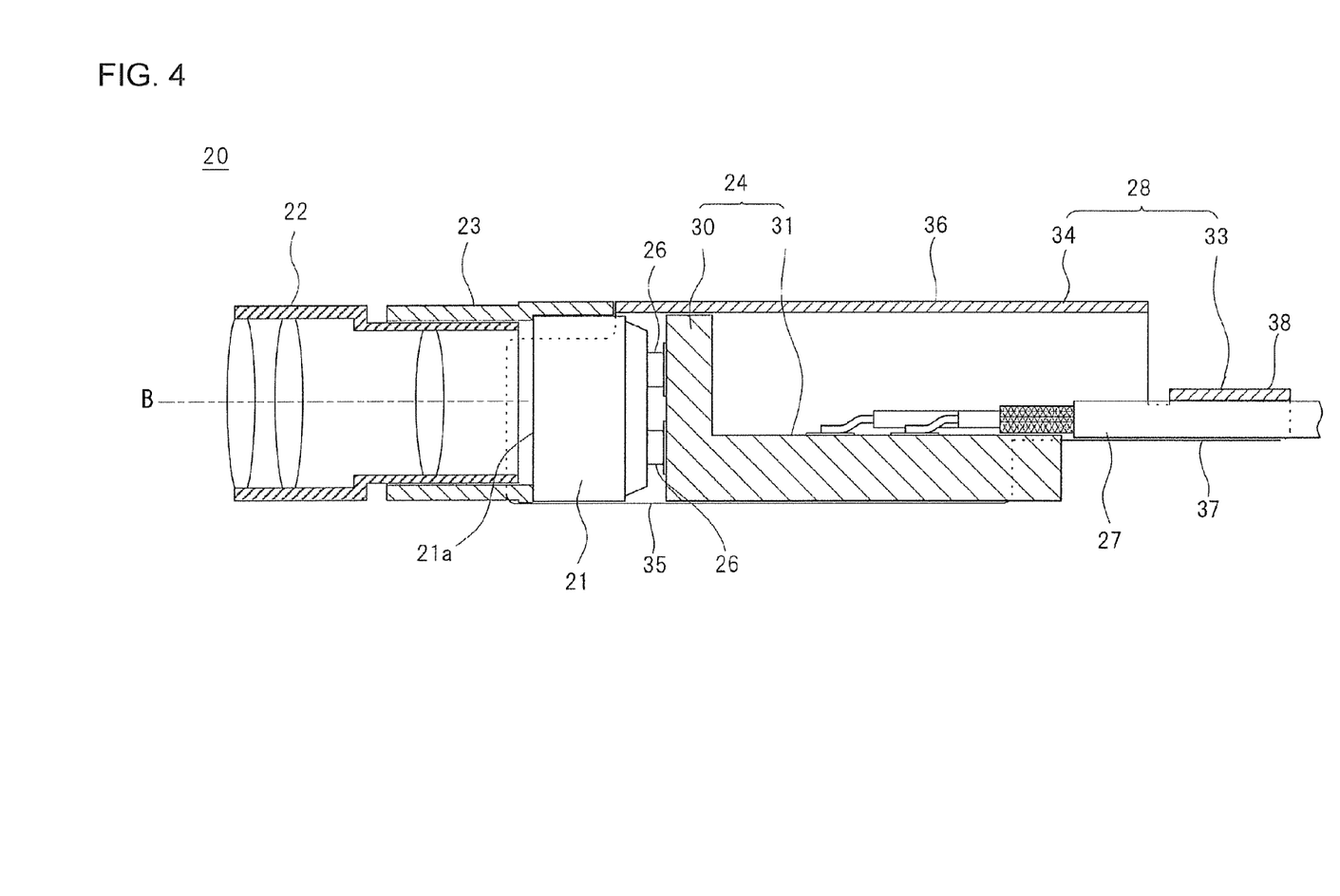
FIG. 4 is a sectional view showing the imaging device in FIG. 2.

FIG. 2 to FIG. 4 show the configuration of the imaging device mounted on the front end portion 10 of the insertion portion 6.

An imaging device 20 has an image sensor 21 such as a CCD (Charge Coupled Device) image sensor or a CMOS (Complementally Metal Oxide Semiconductor) image sensor, a lens barrel 22 receiving an imaging optical system for forming an image of a subject on an image receiving surface 21a of the image sensor 21, a sensor holder 23 holding the image sensor 21 and the lens barrel 22, and a circuit board 24 mounted with the image sensor 21.

The sensor holder 23 holds the lens barrel 22 movably along an optical axis B of the imaging optical system. The lens barrel 22 can be moved to adjust the position of the image sensor 21 relative to the imaging optical system. The lens barrel 22 is fixed to the sensor holder 23, for example, by a bonding agent or the like after the image sensor 21 is positioned.

A plurality of terminals 26 through which signals and electric power are inputted and outputted are provided on the back surface opposite to the image receiving surface 21a of the image sensor 21.

The circuit board 24 mounted with the image sensor 21 has a sensor connection portion 30 and an electric wire connection portion 31.

A plurality of lands are formed in the sensor connection portion 30. The sensor connection portion 30 is attached to the back surface of the image sensor 21. The terminals 26 provided in the back surface of the image sensor 21 are connected to the lands of the sensor connection portion 30.

In the illustrated example, the circuit board 24 is a rigid circuit board. The sensor connection portion 30 and the electric wire connection portion 31 are substantially perpendicular to each other. The connection portion 30 attached to the back surface of the image sensor 21 is disposed in parallel to the image receiving surface 21a of the image sensor 21, while the electric wire connection portion 31 is disposed substantially perpendicularly to the image receiving surface 21a so as to extend in a normal direction of the image receiving surface 21a behind the image sensor 21. Incidentally, the circuit board 24 may be a flexible circuit board.

A plurality of lands 32 are also formed in the electric wire connection portion 31. Central conductors exposed at front end parts of terminal portions of electric wires 27 arranged in a flat shape along the board surface of the electric wire connection portion 31 are connected to the lands 32 of the electric wire connection portion 31 respectively. The circuit board 24 and the image sensor 21 mounted on the circuit board 24 are connected to the processor unit 4 through the electric wires 27.

A retention member 28 for retaining the electric wires 27 connected to the lands 32 of the electric wire connection portion 31 respectively are attached to the circuit board 24. The retention member 28 has a retention portion 33 retaining the electric wires 27, and a cover portion 34 covering the circuit board 24.

The cover portion 34 is constituted by a pair of side walls 35, and a ceiling wall 36 laid between the side walls 35.

The pair of side walls 35 are put on a pair of side surfaces of the circuit board 24 along the normal line of the image receiving surface 21a of the image sensor 21 respectively. The pair of side walls 35 are, for example, bonded and fixed to the pair of side surfaces of the circuit board 24 respectively. The ceiling wall 36 covers the board surface of the circuit board 24 where the lands 32 of the electric wire connection portion 31 are formed, and the terminal portions of the electric wires 27 connected to the lands 32.

The retention portion 33 is constituted by a pair of extension side walls 37 provided on the pair of side walls 35 of the cover portion 34 respectively. The pair of extension side walls 37 extend behind the cover portion 34 along the normal line of the image receiving surface 21a of the image sensor 21. The pair of extension side walls 37 are disposed so that the electric wires 27 arranged in a flat shape along the board surface of the electric wire connection portion 31 of the circuit board 24 are put between the extension side walls 37 in the arrangement direction thereof.

Pressing pieces 38 are provided in the front end portions of the pair of extension side walls 37 respectively. The pressing pieces 38 are disposed to overlap with the electric wires 27 put between the pair of extension side walls 37, from the opposite side to the board surface of the electric wire connection portion 31. As a result, the flat arrangement of the electric wires 27 on the board surface of the electric wire connection portion 31 can be also kept at the rear of the electric wire connection portion 31.

The pressing pieces 38 overlapping with the electric wires 27 are disposed more closely to the electric wire connection portion 31 than the ceiling wall 36 of the cover portion 34. Thus, a step is formed between each pressing piece 38 and the ceiling wall 36.

Figure 5:
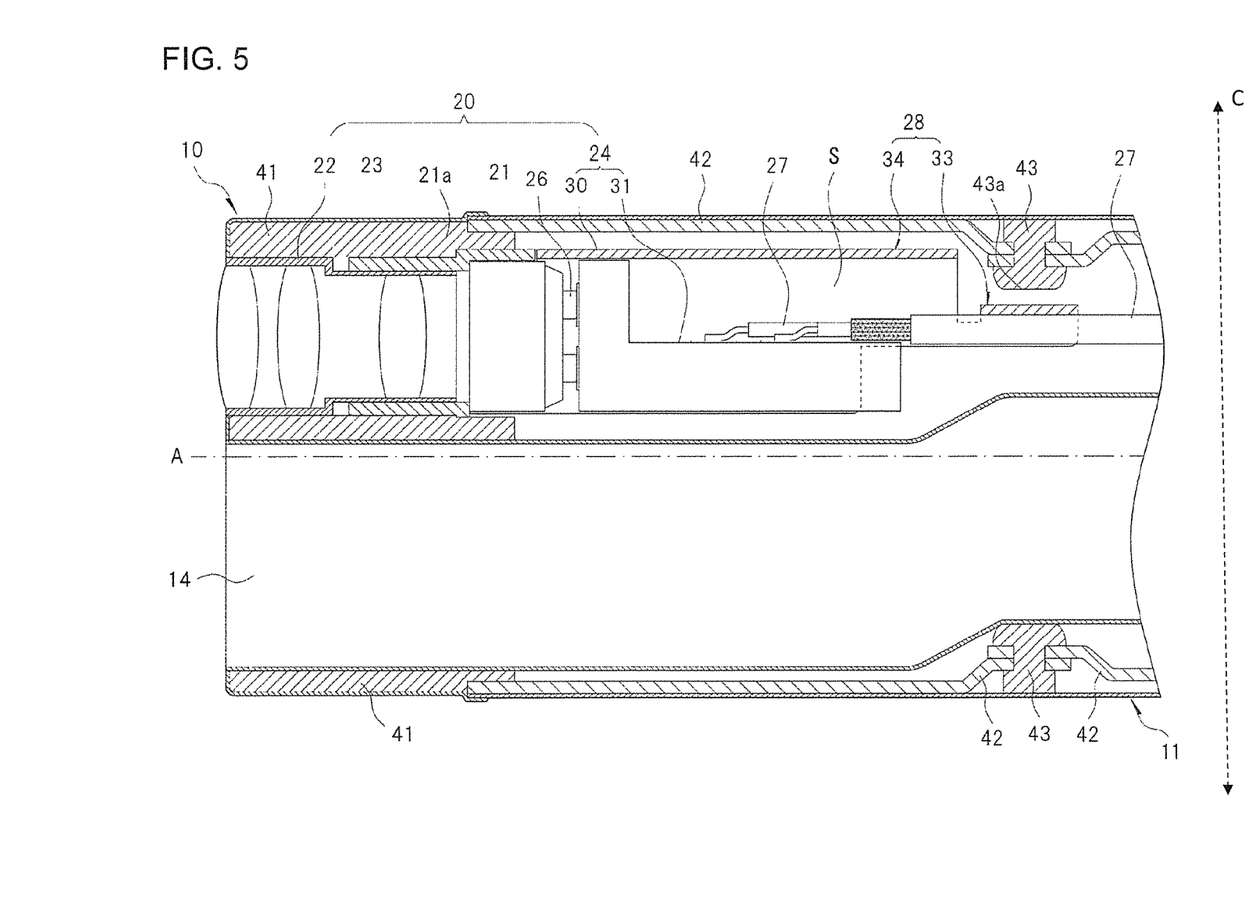
FIG. 5 is a cross-sectional view showing the front end portion and a bent portion of the insertion portion of the endoscope in FIG. 1.
Figure 6:
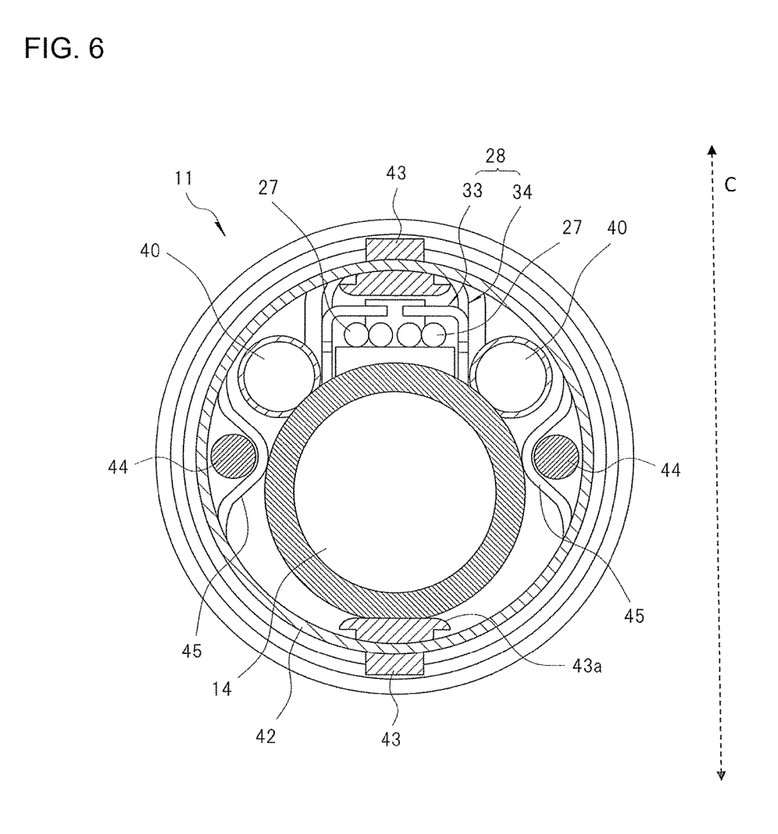
FIG. 6 is a longitudinally sectional view showing the front end portion and the bent portion of the insertion portion of the endoscope in FIG. 1.

FIG. 5 and FIG. 6 show the configuration of the front end portion 10 of the insertion portion 6 mounted with the imaging device 20, and the configuration of the bent portion 11.

The aforementioned imaging device 20, and a front end portion of the treatment tool channel 14 are provided in the front end portion 10. In addition, an illumination optical system for emitting illumination light guided from the light source unit 3 through a light guide 40, etc. are also provided.

The sensor holder 23 holding the image sensor 21 and the lens barrel 22 is received in a reception hole formed in a front end hard portion 41, and fixed to the front end hard portion 41. The front end hard portion 41 is made of a metal material such as a stainless steel material. The front end portion of the treatment tool channel 14 and the illumination optical system are also received in reception holes formed in the front end hard portion 41 respectively, and fixed to the front end hard portion 41.

The image receiving surface 21a of the image sensor 21 held by the sensor holder 23 fixed to the front end hard portion 41 is disposed substantially perpendicularly to the longitudinal axis A of the insertion portion 6. The electric wire connection portion 31 substantially perpendicular to the image receiving surface 21a is disposed along the longitudinal axis A.

The bent portion 11 includes a plurality of annular pieces 42 arranged along the longitudinal axis A. Due to the pieces 42, the bent portion 11 is arranged as a tubular body that can receive the electric wires 27 connected to the circuit board 24 of the imaging device 20, the treatment tool channel 14, the light guide 40, etc.

Two pieces 42 adjacent to each other are connected to each other rotatably around an axis substantially perpendicular to the longitudinal axis A by a pair of pins 43 disposed on the axis. Individual rotations between such adjacent two pieces 42 are combined so that the bent portion 11 can be bent as a whole.

The bent portion 11 is operated by a pair of wires 44 inserted into the bent portion 11 from the operation portion 7 through the soft portion 12 (see FIG. 1). By operation on the operation portion 7, of the pair of wires 44, one wire 44 is pulled while the other wire 44 is paid out. Thus, the bent portion 11 is operated and bent.

Of the pieces 42 constituting the bent portion 11, the leading piece 42 on the front end portion 10 side is joined to the front end hard portion 41 of the front end portion 10. Thus, the front end portion 10 and the bent portion 11 are connected. The circuit board 24 of the imaging device 20 in which the sensor holder 23 is fixed to the front end hard portion 41, and the retention member 28 attached to the circuit board 24 are disposed inside the leading piece 42 which is a part in the insertion portion 6 and adjacent to the front end portion 10 in the axial direction of the insertion portion 6.

Of each of the pair of pins 43 connecting the leading piece 42 with the piece 42 adjacent to the leading piece 42, a head portion 43a protrudes on the inner diameter side of the pieces 42. The distance between the pair of pins 43 is narrowed in the facing direction C of the pair of pins 43 perpendicular to the axial direction of the insertion portion 6 so that a narrowed section can be formed between the pins 43. The inner diameter of the insertion portion 6 in the narrowed section in a direction parallel to the facing direction C of the pins 43 is smaller than that of any other section in front or at the rear of the disposed section of the pair of pins 43 in the axial direction of the insertion portion 6.

The retention portion 33 of the retention member 28 disposed inside the leading piece 42 is disposed between the pair of pins 43 forming the narrowed section inside the insertion portion 6 so as to retain the electric wires 27 connected to the electric wire connection portion 31 of the circuit board 24.

As described above, the electric wires 27 are retained by the retention portion 33 so as to keep their arrangement on the board surface of the electric wire connection portion 31 and to be tied up in a flat shape. The board surface of the electric wire connection portion 31 is disposed substantially perpendicularly to the facing direction C of the pair of pins 43 holding the retention portion 33 therebetween. Accordingly, the electric wires 27 retained to be tied up in a flat shape by the retention portion 33 is tied up to be longer in a direction perpendicular to the facing direction (narrowing direction) C of the pins 43 than in the facing direction C.

In this manner, the electric wires 27 are tied up into a flat shape to be longer in a direction perpendicular to the narrowing direction and the axial direction of the insertion portion 6 than in the narrowing direction between the pair of pins 43 forming the narrowed section. Thus, the width of the bundle of the electric wires 27 in the narrowing direction can be reduced in comparison with a case where the electric wires 27 are, for example, tied up in a columnar shape. It is therefore possible to narrow the gap between the imaging device 20 and the inner circumferential surface of the piece 42 to thereby reduce the diameter of the insertion portion 6. In addition, the electric wires 27 are restrained by one another so that the electric wires 27 can be suppressed from being damaged by contact with the pins 43.

In addition, in the embodiment, the retention member 28 including the retention portion 33 is fixed to the circuit board 24. Accordingly, displacement of the electric wires 27 relative to the electric wire connection portion 31 between the retention portion 33 and the electric wire connection portion 31 of the circuit board 24 can be suppressed to enhance the durability of connection between the electric wires 27 and the lands 32 of the electric wire connection portion 31.

In order to enhance the durability of connection between the electric wires 27 and the lands 32 of the electric wire connection portion 31, a resin material may be charged into a space S surrounded by the pair of side walls 35 and the ceiling wall 36 of the cover portion 34 of the retention member 28 and the electric wire connection portion 31 of the circuit board 24. Since the terminal portions of the electric wires 27 connected to the lands 32 of the electric wire connection portion 31 are embedded in the resin material to thereby further suppress the displacement of the electric wires 27 relative to the electric wire connection portion 31, the durability of connection between the electric wires 27 and the lands 32 of the electric wire connection portion 31 can be further enhanced. In addition, fixing strength of the retention member 28 to the circuit board 24 can be also enhanced.

Incidentally, although description has been made on the assumption that the narrowed section inside the insertion portion 6 is provided between the pair of pins 43, the narrowed section may be, for example, provided between respective fixation portions 45 for the pair of wires 44 in the leading piece 42. The fixation portions 45 are formed as follows. That is, due to two slits extending in parallel to the circumferential direction, the leading piece 42 is cut out partially to form bridge pieces. The bridge pieces are swollen to the inner diameter side of the piece 42 by raising or the like. Thus, a distance between the pair of fixation portions 45 is also narrowed in the facing direction C of the pair of fixation portions 45 perpendicular to the axial direction of the insertion portion 6 in the same manner as the distance between the pair of pins 43, so that a narrowed section can be formed between the fixation portions 45. The inner diameter of the insertion portion 6 in the narrowed section in a direction parallel to the facing direction C is smaller than that of any other section in front or at the rear of the disposed section of the pair of fixation portions 45 in the axial direction of the insertion portion 6. Accordingly, the retention portion 33 of the retention member 28 may be disposed between the pair of fixation portions 45 so that the electric wires 27 can be tied up in a flat shape longer in a direction perpendicular to the narrowing direction C and the axial direction of the insertion portion 6 than in the narrowing direction C between the pair of fixation portions 45. It is therefore possible to narrow the gap between the imaging device 20 and the inner circumferential surface of the piece 42 to thereby reduce the diameter of the insertion portion 6. In addition, the electric wires 27 can be suppressed from being damaged by contact with the fixation portions 45.

In addition, although description has been made in the illustrated example on assumption that the number of electric wires 27 connected to the electric wire connection portion 31 of the circuit board 24 is four, and the electric wires 31 are tied up in a flat shape by the retention portion 33, the shape is not limited to the flat shape. It will go well only if the shape is longer in a direction perpendicular to the narrowing direction of the narrowed section than in the narrowing direction. When the number of electric wires 27 is, for example, six, the electric wires 27 may be tied up so that two electric wires 27 can be arrayed in the narrowing direction and three electric wires 27 can be arrayed in a direction perpendicular to the narrowing direction.

Figure 7:
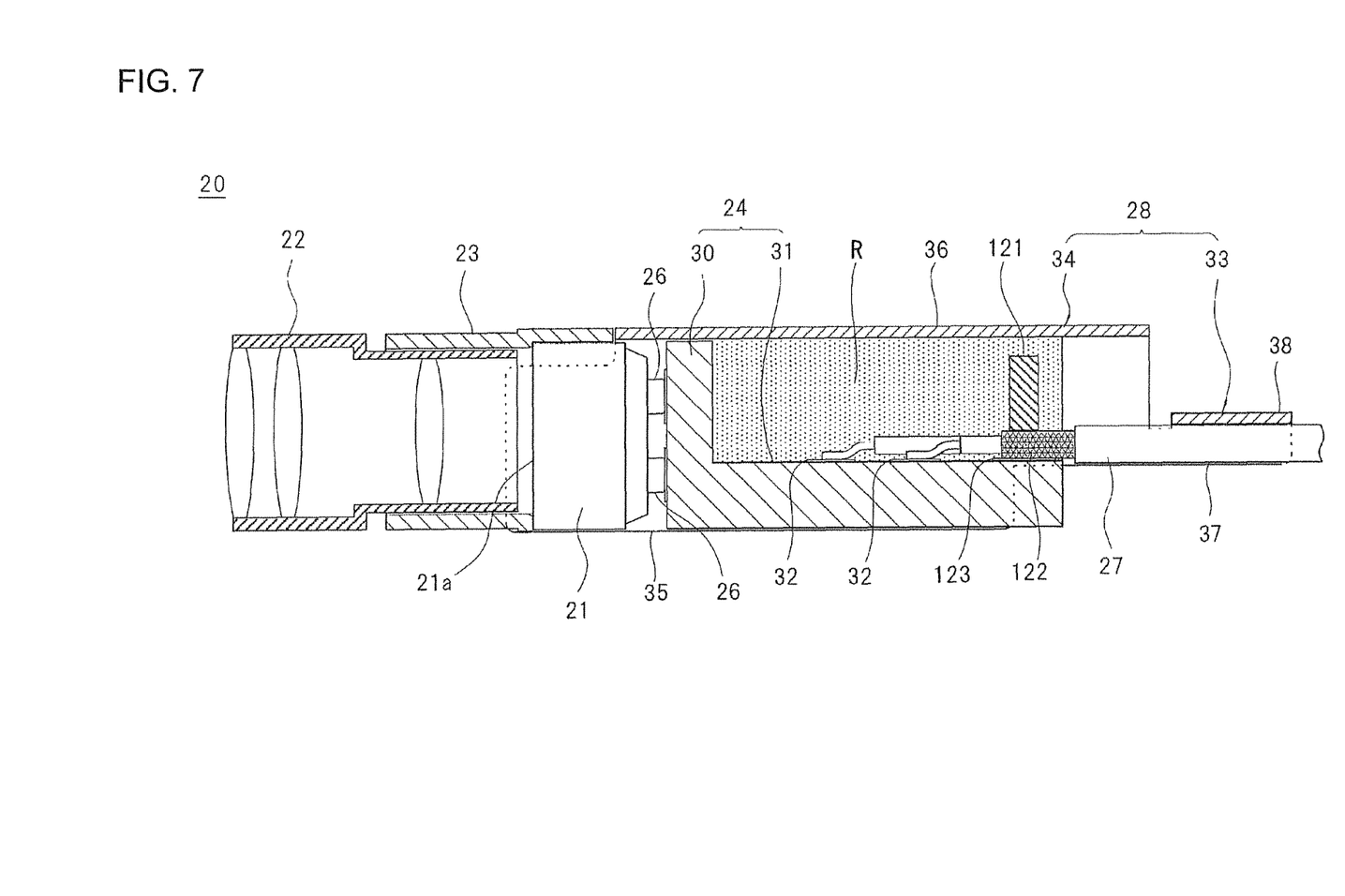
FIG. 7 is a sectional view showing another example of an imaging device mounted on a front end portion of an insertion portion of an endoscope for explaining an embodiment of the invention.
Figure 8:
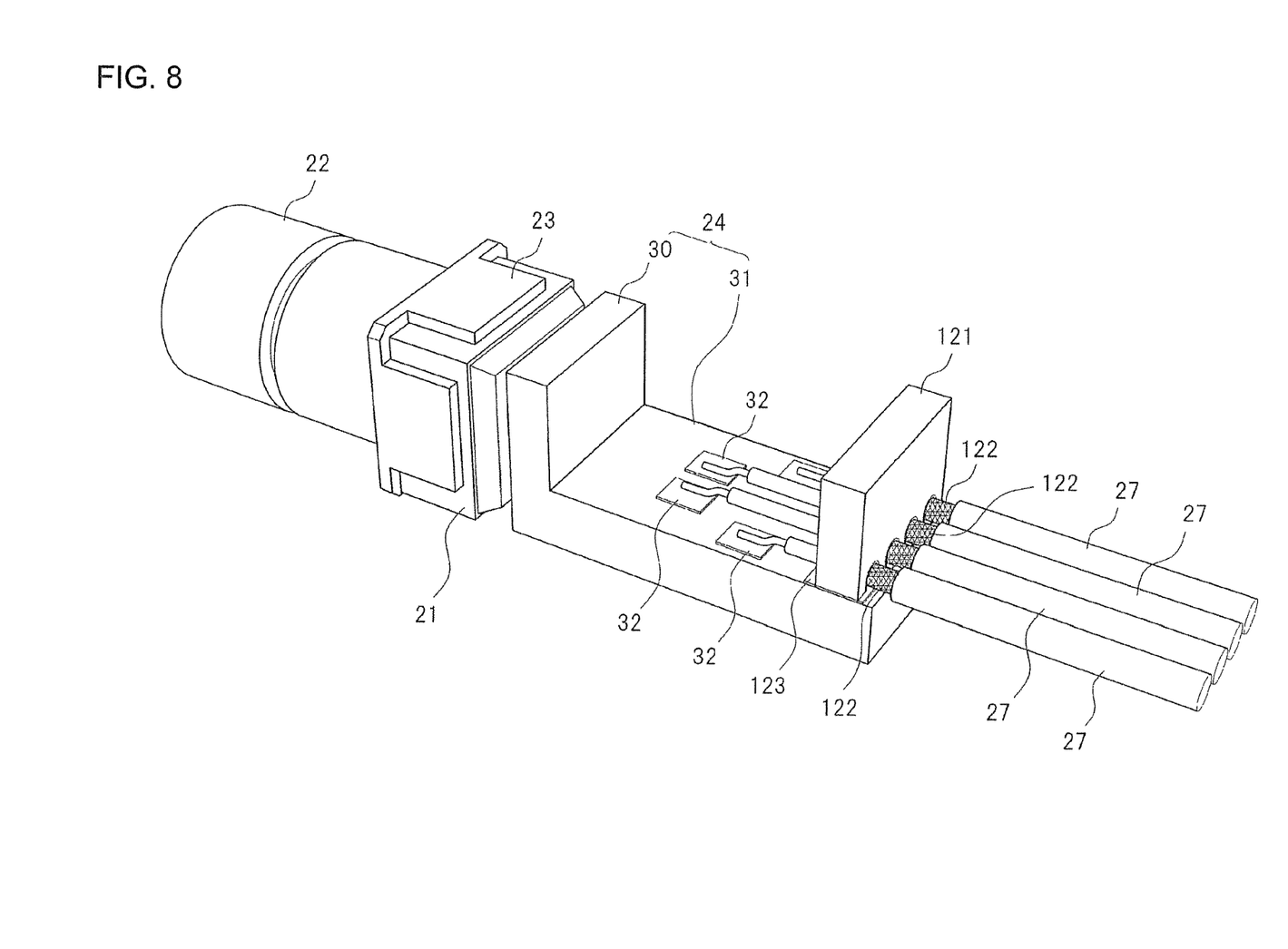
FIG. 8 is a perspective view showing the inside of the imaging device in FIG. 7.
Figure 9:
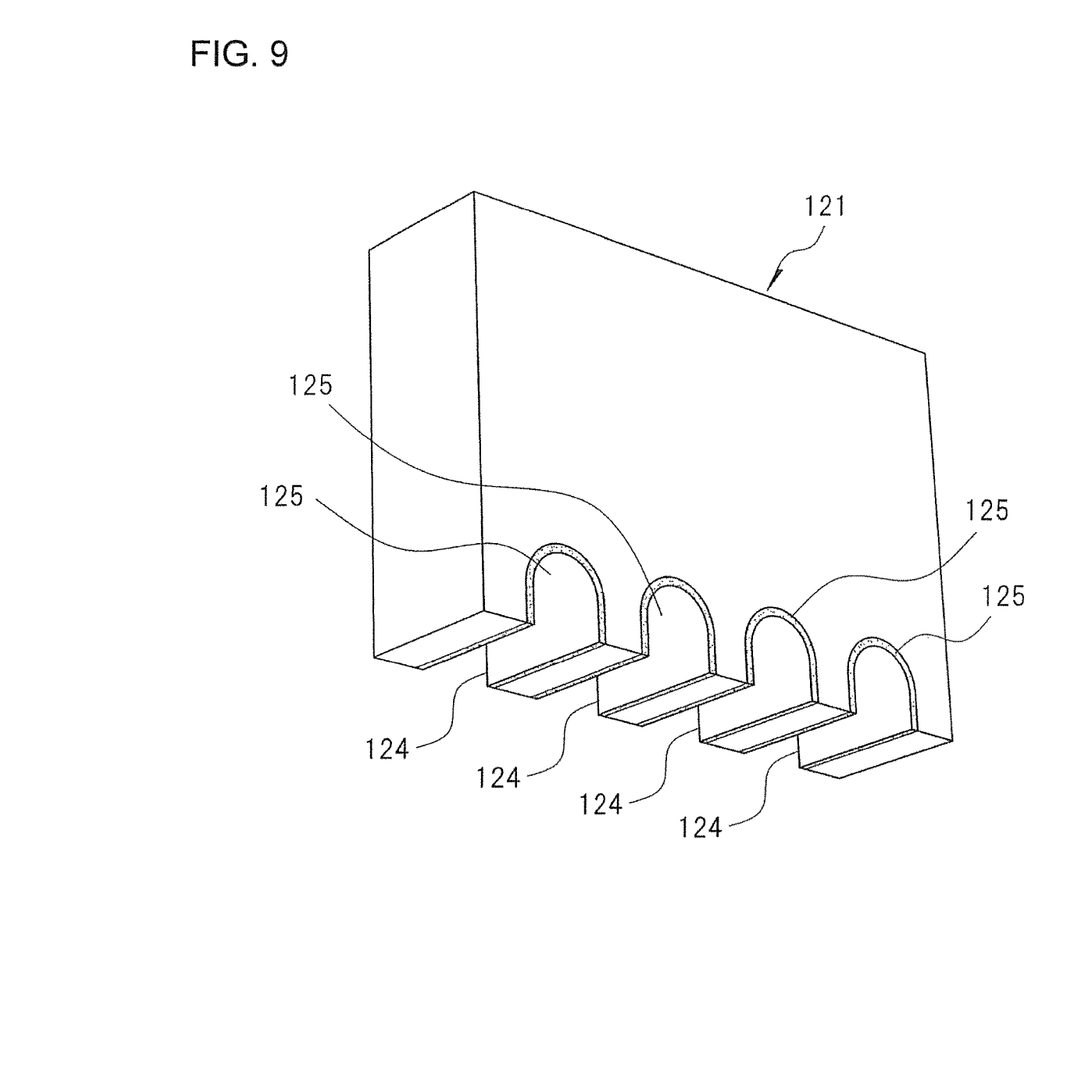
FIG. 9 is a perspective view showing a connection auxiliary member of the imaging device in FIG. 7.

FIG. 7 to FIG. 9 show another example of an imaging device mounted on a front end portion of an insertion portion of an endoscope in order to explain an embodiment of the invention. Incidentally, elements that can be shared with those in the aforementioned imaging device 20 are referenced correspondingly, and description thereof will be omitted or simplified.

An imaging device 120 shown in FIG. 7 to FIG. 9 further includes a connection auxiliary member 121. The connection auxiliary member 121 is disposed so that respective terminal portions of a plurality of electric wires 27 arranged along a board surface of an electric wire connection portion 31 of a circuit board 24 are put between the connection auxiliary member 121 and the electric wire connection portion 31.

In this example, each of the electric wires 27 is a shield wire, in which a shield conductor 122 is exposed at a base end part of the terminal portion of the electric wire 27, and a central conductor to be connected to a land 32 of the electric wire connection portion 31 is exposed more closely to the front end of the electric wire 27 than the shield conductor 122.

In the electric wire connection portion 31, lands 123 are formed so that the shield conductors 122 of the electric wires 27 arranged along the board surface of the electric wire connection portion 31 can be connected to the lands 123 respectively. The shield conductors 122 of the electric wires 27 are connected to the lands 123 so that the shield conductors 122 can have the same potential as the lands 123 respectively. Since the shield conductors 122 of the electric wires 27 are connected to the lands 123, the durability of connection between the central conductors of the electric wires 27 disposed more closely to the front end than the shield conductors 122 and the lands 32 of the electric wire connection portion 31 can be enhanced.

The connection auxiliary member 121 is disposed so that the base end parts of the terminal portions of the electric wires 27 whose shield conductors 122 have been exposed are put between the connection auxiliary member 121 and the electric wire connection portion 31.

A plurality of notches 124 are formed in the opposed surface of the connection auxiliary member 121 to the electric wire connection portion 31 so that the base end parts of the terminal portions of the electric wires 27 arranged in a flat shape along the board surface of the electric wire connection portion 31 can be fitted into the notches 124 respectively. Metal foil 125 is formed on the bottom surface of each of the notches 124.

For example, the connection auxiliary member 121 can be formed using a resin material such as glass epoxy, and the metal foil 125 can be formed using MID (Molded Interconnect Device) technology for forming a circuit pattern on a surface of a three-dimensional structure.

The base end parts of the terminal portions of the electric wires 27 are received respectively in the notches 124 of the connection auxiliary member 121 disposed in the electric wire connection portion 31, so that the metal foils 125 covering the bottom surfaces of the notches 124 can touch the shield conductors 122 exposed at the base end parts of the terminal portions of the electric wires 27 respectively. The shield conductors 122 exposed at the base end parts of the terminal portions of the electric wires 27 are soldered with the metal foils (contact portions) 125 respectively. Thus, the connection auxiliary member 121 is joined to the base end parts of the terminal portions of the respective electric wires 27.

The connection auxiliary member 121 joined to the base end parts of the terminal portions of the respective electric wires 27 is fixed to a retention member 28 fixed to the circuit board 24. In this example, a resin material R is charged into a space surrounded by a pair of side walls 35 and a ceiling wall 36 of a cover portion 34 of the retention member 28 and the electric wire connection portion 31 of the circuit board 24. The connection auxiliary member 121 is embedded in the resin material R together with the terminal portions of the electric wires 27. Thus, the connection auxiliary member 121 is fixed to the retention member 28.

As described above, the terminal portions of the electric wires 27 are embedded in the resin material R so that the durability of connection between the electric wires 27 and the lands 32 of the electric wire connection portion 31 can be enhanced. Further, since the connection auxiliary member 121 integrated with the electric wires 27 is embedded in the resin material R, the connection auxiliary member 121 is locked to the retention member 28 in the longitudinal direction of the electric wires 27. Thus, longitudinal displacement of the terminal portions of the electric wires 27 can be more surely suppressed so that the durability of connection between the electric wires 27 and the lands 32 of the electric wire connection portion 31 can be further enhanced. For example, fluororesin with high insulation and low dielectric is used for coating on the electric wires 27. Fluororesin is generally a hardly adhesive material. Even when the terminal portions of the electric wires 27 in which such hardly adhesive coating is left behind are fixed, satisfactory strength can be obtained by use of the connection auxiliary member 121.

Figure 10:
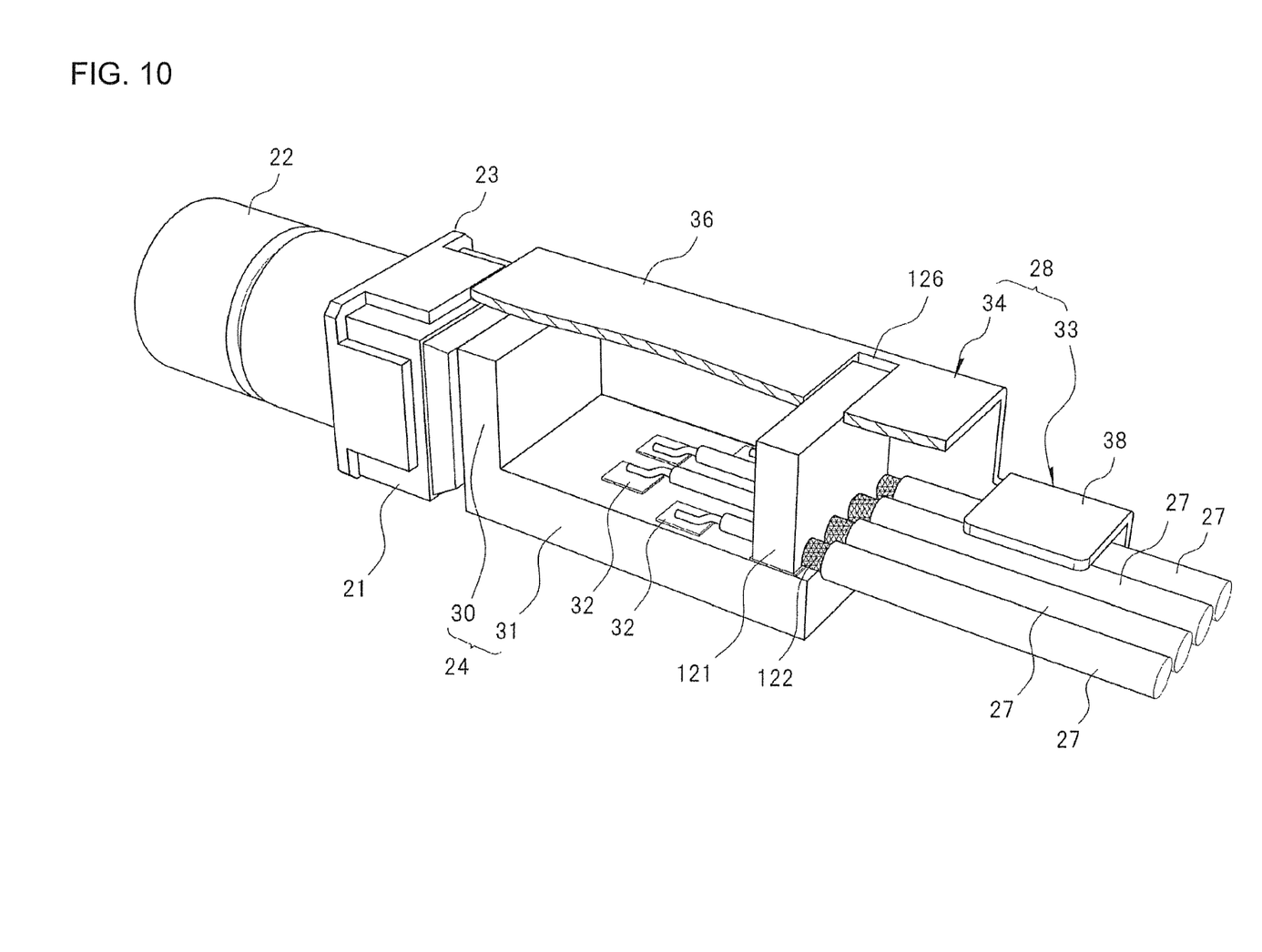
FIG. 10 is a perspective view showing a modification of the imaging device in FIG. 7.

FIG. 10 shows a modification of the aforementioned imaging device 120.

In the example shown in FIG. 10, a lock hole 126 is formed in the ceiling wall 36 extending along the electric wires 27 in the cover portion 34 of the retention member 28 so that the connection auxiliary member 121 can be inserted and locked to the lock hole 126. Also in this example, the connection auxiliary member 121 can be locked to the retention member 28 in the longitudinal direction of the electric wires 27. Thus, longitudinal displacement of the terminal portions of the electric wires 27 can be suppressed more surely, so that the durability of connection between the electric wires 27 and the lands 32 of the electric wire connection portion 31 can be enhanced.

As has been described above, an endoscope disclosed in the present specification includes: an image sensor that is disposed at a front end portion of an insertion portion; a circuit board that is mounted with the image sensor; a plurality of electric wires that are connected to the circuit board; and a retention member that includes a retention portion tying up the electric wires; wherein: the retention portion is disposed in a narrowed section that is provided in the insertion portion and inside a part adjacent to the front end portion in an axial direction of the insertion portion and narrowed in a narrowing direction perpendicular to the axial direction so that the electric wires are tied up to be longer in a direction perpendicular to the narrowing direction and the axial direction than in the narrowing direction.

In addition, in the endoscope disclosed in the present specification, the retention member may be fixed to the circuit board.

In addition, the endoscope disclosed in the present specification may further include a connection auxiliary member that is disposed so that base end parts of terminal portions of the electric wires arranged along a board surface of the circuit board are provided between the connection auxiliary member and the circuit board, the terminal portions including central conductors exposed at front end parts of the terminal portions respectively, the base end parts excluding the central conductors respectively; wherein the connection auxiliary member includes a plurality of notches that receive the base end parts of the terminal portions of the electric wires respectively, and the connection auxiliary member is joined to the base end parts of the terminal portions of the electric wires received in the notches respectively, and fixed to the retention member.

In addition, in the endoscope disclosed in the present specification, the electric wires may be shield wires; contact portions of the connection auxiliary member, which contact with the terminal portions respectively, may be formed with metal; and the contact portions may be soldered with the shield conductors exposed at the terminal portions of the electric wires respectively.

In addition, in the endoscope disclosed in the present specification, the retention member may further include a cover portion that covers the circuit board and the terminal portions of the electric wires connected to the circuit board; a gap between the cover portion and the circuit board covered with the cover portion may be filled with a resin material; and the connection auxiliary member may be embedded in the resin material.

In addition, in the endoscope disclosed in the present specification, the retention member may include a wall portion extending along the electric wires; and the connection auxiliary member may be inserted and locked to a hole formed in the wall portion.

In addition, in the endoscope disclosed in the present specification, the insertion portion may include a bent portion that is provided continuously to the front end portion; the bent portion may include a plurality of pieces that are disposed to be arrayed in a longitudinal direction of the insertion portion; and the narrowed section may be located between a pair of pins that connect adjacent two of the pieces with each other rotatably.

In addition, in the endoscope disclosed in the present specification, an outer shape of the image sensor may be not larger than 1 mm square in view along a normal direction of an image receiving surface of the image sensor.

Although the invention has been described above in relation to preferred embodiments and modifications thereof, it will be understood by those skilled in the art that other variations and modifications can be effected in these preferred embodiments without departing from the scope and spirit of the invention.

What is claimed is:

1. An endoscope comprising:
an image sensor that is disposed at a front end portion of an insertion portion of the endoscope;
a circuit board that is mounted with the image sensor;
a plurality of electric wires that are electrically connected to the circuit board;
a connection auxiliary member that is disposed so that base end parts of terminal portions of the electric wires arranged along a board surface of the circuit board are provided between the connection auxiliary member and the circuit board, the terminal portions including central conductors exposed at front end parts of the terminal portions respectively, the base end parts excluding the central conductors respectively; and
a retention member that has a retention portion tying up the electric wires; wherein:
the retention member is fixed to the circuit board;
the retention portion is disposed in a narrowed section that is provided in the insertion portion and inside a part adjacent to the front end portion in an axial direction of the insertion portion and narrowed in a narrowing direction perpendicular to the axial direction so that the electric wires are tied up to be longer in a direction perpendicular to the narrowing direction and the axial direction than in the narrowing direction, the electric wires are shield wires in which the central conductors are surrounded by shield conductors respectively;

contact portions of the connection auxiliary member, which contact with the terminal portions respectively, are formed with metal; and the contact portions are soldered with the shield conductors exposed at the terminal portions of the electric wires respectively.

2. The endoscope according to claim 1, further comprising:

the connection auxiliary member comprises a plurality of notches that receive the base end parts of the terminal portions of the electric wires respectively, and the connection auxiliary member is joined to the base end parts of the terminal portions of the electric wires received in the notches respectively, and fixed to the retention member.

3. The endoscope according to claim 2, wherein:

the retention member further comprises a cover portion that covers the circuit board and the terminal portions of the electric wires connected to the circuit board;

a gap between the cover portion and the circuit board covered with the cover portion is filled with a resin material; and the connection auxiliary member is embedded in the resin material.

4. The endoscope according to claim 3, wherein:

the insertion portion comprises a bent portion that is provided continuously to the front end portion;

the bent portion comprises a plurality of pieces that are arranged to be arrayed in a longitudinal direction of the insertion portion; and the narrowed section is located between a pair of pins that connect adjacent two of the pieces with each other rotatably.

5. The endoscope according to claim 3, wherein an area of an outer shape of the image sensor is not larger than 1 mm square in view along a normal direction of an image receiving surface of the image sensor.

6. The endoscope according to claim 2, wherein:

the retention member comprises a wall portion extending along the electric wires; and the connection auxiliary member is inserted and locked to a hole formed in the wall portion.

7. The endoscope according to claim 6, wherein:

the insertion portion comprises a bent portion that is provided continuously to the front end portion;

the bent portion comprises a plurality of pieces that are arranged to be arrayed in a longitudinal direction of the insertion portion; and the narrowed section is located between a pair of pins that connect adjacent two of the pieces with each other rotatably.

8. The endoscope according to claim 6, wherein an area of an outer shape of the image sensor is not larger than 1 mm square in view along a normal direction of an image receiving surface of the image sensor.

9. The endoscope according to claim 2, wherein:

the insertion portion comprises a bent portion that is provided continuously to the front end portion;

the bent portion comprises a plurality of pieces that are arranged to be arrayed in a longitudinal direction of the insertion portion; and the narrowed section is located between a pair of pins that connect adjacent two of the pieces with each other rotatably.

10. The endoscope according to claim 2, wherein an area of an outer shape of the image sensor is not larger than 1 mm square in view along a normal direction of an image receiving surface of the image sensor.

11. The endoscope according to claim 1, wherein:

the retention member further comprises a cover portion that covers the circuit board and the terminal portions of the electric wires connected to the circuit board;

a gap between the cover portion and the circuit board covered with the cover portion is filled with a resin material; and the connection auxiliary member is embedded in the resin material.

12. The endoscope according to claim 1, wherein:

the retention member comprises a wall portion extending along the electric wires; and the connection auxiliary member is inserted and locked to a hole formed in the wall portion.

13. The endoscope according to claim 1, wherein:

the insertion portion comprises a bent portion that is provided continuously to the front end portion;

the bent portion comprises a plurality of pieces that are arranged to be arrayed in a longitudinal direction of the insertion portion; and the narrowed section is located between a pair of pins that connect adjacent two of the pieces with each other rotatably.

14. The endoscope according to claim 1, wherein:

the insertion portion comprises a bent portion that is provided continuously to the front end portion;

the bent portion comprises a plurality of pieces that are arranged to be arrayed in a longitudinal direction of the insertion portion; and the narrowed section is located between a pair of pins that connect adjacent two of the pieces with each other rotatably.

15. The endoscope according to claim 1, wherein:

the insertion portion comprises a bent portion that is provided continuously to the front end portion;

the bent portion comprises a plurality of pieces that are arranged to be arrayed in a longitudinal direction of the insertion portion; and the narrowed section is located between a pair of pins that connect adjacent two of the pieces with each other rotatably.

16. The endoscope according to claim 1, wherein an area of an outer shape of the image sensor is not larger than 1 mm square in view along a normal direction of an image receiving surface of the image sensor.

* * * * *